United States Patent [19]

Coss et al.

[11] Patent Number: 4,876,256
[45] Date of Patent: Oct. 24, 1989

[54] ALKYLPIPERAZINYLPYRIDINES AS HYPOGLYCEMIC AGENTS

[75] Inventors: Malcolm M. Coss, Freehold; Richard L. Tolman, Warren, both of N.J.

[73] Assignee: Merck & Co., Inc., Rahway, N.J.

[21] Appl. No.: 188,246

[22] Filed: Apr. 29, 1988

[51] Int. Cl.$^4$ .................. A61K 31/495; A61K 31/44; C07D 401/04
[52] U.S. Cl. ..................................... 514/252; 544/360
[58] Field of Search .......................... 544/360; 514/252

[56] References Cited

U.S. PATENT DOCUMENTS 3,773,951 11/1973 Rodriguez ........................... 424/250
3,948,898  4/1976 Kutter et al. ........................ 260/268
4,017,622  4/1977 Minami et al. ...................... 424/250

FOREIGN PATENT DOCUMENTS 177392 4/1986 European Pat. Off. ............ 544/360

OTHER PUBLICATIONS

Saari et al., J. Med. Chem. 26, 1696 (1983) "Pyridinylpiperazines, a New Class of Selective α, -Adrenoceptor Antagonists".
Pinder, Drugs of the Future, vol. 10, 841 (1985).
Soda et al., Chem. Abst. 109694w "Dicarboxylic acid imides".

*Primary Examiner*—Celilia Shen
*Attorney, Agent, or Firm*—Melvin Winokur; Joseph F. DiPrima

[57] ABSTRACT

Alkylpiperazinylpyridines of formula (I) are disclosed as hypoglycemic agents.

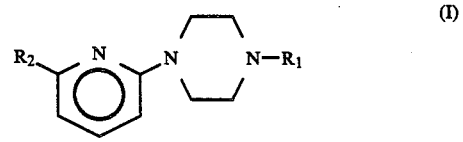

5 Claims, No Drawings

ALKYLPIPERAZINYLPYRIDINES AS HYPOGLYCEMIC AGENTS

BACKGROUND OF THE INVENTION

Diabetes is a condition characterized by abnormal insulin secretion and a variety of metabolic and vascular manifestations reflected in a tendency toward inappropriately elevated blood glucose levels and which if left poorly treated or untreated can result in accelerated, nonspecific atherosclerosis, neuropathy and thickened capillary lamina causing renal and retinal impairment. Diabetes is characterized as being insulin dependent (Type I) and non-insulin dependent (Type II). Type I diabetes is due to damage and eventual loss of the β-cells of the pancreatic islets of Langerhans with a resulting loss of insulin production. Type II diabetics secrete insulin, however, the insulin is somehow not properly or effectively utilized in the metabolism of blood sugars and glucose accumulates in the blood to above normal levels. This condition is termed insulin resistance.

With the certainty of serious complications resulting from high glucose levels in poorly controlled or uncontrolled diabetics, means to lower blood glucose have been research goals for a considerable period of time. With Type I diabetes glucose control can only be achieved with daily insulin injections. With Type II diabetes glucose control can be effected from a combination of diet and drugs which lower glucose levels. The currently available oral hypoglycemic agents are not completely satisfactory since they may not offer complete blood glucose control or may provide a variety of undesirable side effects or they may elevate insulin concentrations to undesirable and dangerous levels. Thus, the search for improved oral hypoglycemic agents is a continuing one.

The compounds of the present invention are substituted pyridines. The literature discloses a number of substituted pyridines which in some cases are structurally similar to the present compounds; however no suggestion is made of hypoglycemic activity.

German Pat. DE No. 2345422 and its U.S. equivalent U.S. Pat No. 3,948,898 disclose 1-(6-Methyl-2-pyridyl)-piperazine (1) and 1-(4-Methyl-2-pyridyl)piperazine (2) as intermediates in the preparation of 2-(piperazinylalkyl)isoquinolinediones

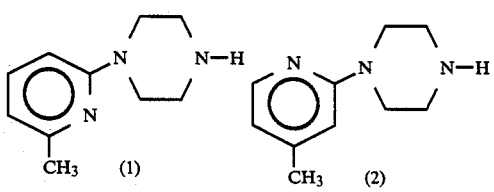

German Pat. DE No. 2362553 and its U.S. equivalent U.S. Pat. No. 4,017,622 disclose 6-(4-methyl-1-piperazinyl)-2-pyridinamine (3) which was used as an intermediate in the preparation of other piperazine derivatives, having antibacterial activities.

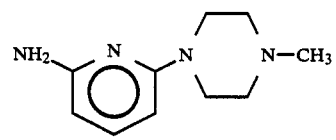

U.S. Pat. No. 3,773,951 discloses 1-(2-pyridyl)piperazine as an antidepressant.

DESCRIPTION OF THE INVENTION

This invention is directed to certain novel pharmaceutical compositions and methods for lowering the blood glucose levels of diabetic or insulin resistant obese patients. The compounds of this invention with novel hypoglycemic activity have the structural formula (I):

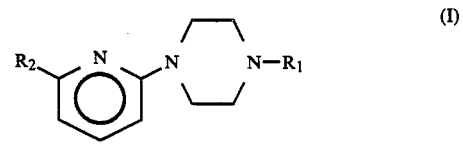

wherein:
$R_1$ = H, $C_{1-6}$alkyl, $C_{2-6}$alkenyl, or $C_{2-6}$alkynyl;
$R_2$ = H, $C_{1-6}$alkyl, $C_{2-6}$alkenyl, or $C_{2-6}$alkynyl.

It should be understood that the alkyl, alkenyl and alkynyl groups of this invention may either be in a straight chain or branched configuration.

One embodiment of the present invention relates to novel pharmaceutical compositions and methods of treating hypoglycemia wherein the therapeutically active ingredient has structural formula (I):

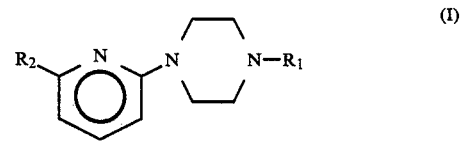

wherein:
$R_1$ = H, $C_{1-6}$alkyl, $C_{2-6}$alkenyl, or $C_{2-6}$alkynyl;
$R_2$ = H, $C_{1-6}$alkyl, $C_{2-6}$alkenyl, or $C_{2-6}$alkynyl.

A second embodiment of the present invention is the novel compounds of structural formula (I):

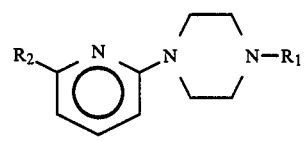

wherein:
$R_1$ = $C_{1-6}$alkyl, $C_{2-6}$alkenyl, or $C_{2-6}$alkynyl;
$R_2$ = H, $C_{1-6}$alkyl, $C_{2-6}$alkenyl, or $C_{2-6}$alkynyl.

In one class of this embodiment are the compounds wherein: $R_1$ is $C_{1-6}$alkyl; and $R_2$ is $C_{1-6}$alkyl.

Exemplifying this class is the compound wherein: $R_1$ is $CH_3$; and $R_2$ is $CH_3$.

Piperazinylpyridines and dipiperazinylpyridines can be prepared by the reaction of the appropriately substituted halopyridines with a N-protected piperazine such as, N-(tert-butoxycarbonyl)piperazine. The protecting group can then be removed by hydrogenation.

Piperazinylpyridines can be substituted on the piperazine nitrogen by treatment with an alkyl, alkenyl or alkynyl halide.

The appropriate alkylhalopyridines are commercially available or may be prepared following the synthetic procedures described in Pyridine and its Derivatives—Part II (1961)—John Wiley & Sons and Volume 14, Supplement Part II (1974)—John Wiley & Sons. In one methodology the methyl group of 2-picoline may be extended to a larger alkyl, alkenyl or alkynyl moiety by taking advantage of the $CH_2$—H bond acidity followed by an alkylation or carbonyl addition reaction to form the appropriate $R_2$ group. The pyridine nitrogen is then converted to the oxide followed by rearrangement to the pyridone, conversion to the alcohol and reaction with $POCl_3$ to yield the alkylchloro-, alkenylchloro- or alkynylchloropyridine.

The compounds of this invention are all readily adapted to therapeutic use as oral hypoglycemic agents. These compounds lower the blood sugar levels of diabetic subjects to a statistically significant degree. For instance, 1-(6-methyl-2-pyridyl)piperazine a typical and preferred agent of the present invention has been found to consistently lower blood sugar levels and improve glucose tolerance in either fasted or fed diabetic (i.e., hyperglycemic) mice to a statistically significant degree when given by the oral route of administration at dose levels ranging from 1 mg/kg to 100 mg/kg, respectively, without showing any toxic side effects. The other compounds of this invention also produce similar results. In general, these compounds are ordinarily administered at dosage levels ranging from about 1 mg to about 100 mg per kg of body weight per day, although variations will necessarily occur depending upon the condition and individual response of the subject being treated and the particular type of oral pharmaceutical formulation chosen.

Administration over time to obese, insulin resistant mice, resulted in a significant reduction of glucose in a glucose tolerance test.

In connection with the use of the compounds of this invention for the treatment of diabetic subjects, it is to be noted that they may be administered either alone or in combination with pharmaceutically acceptable carriers and that such administration can be carried out in both single and multiple dosages. More particularly, the novel compounds of the invention can be administered in a wide variety of different dosage forms, i.e., they may be combined with various pharmaceutically acceptable inert carriers in the forms of tablets, capsules, lozenges, troches, hard candies, powders, aqueous suspension, elixirs, syrups and the like. Such carriers include diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tableting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the fasted or fed hyperglycemic mouse when tested therein for such purposes according to the procedures described by Saperstein et al. as submitted to the journal Metabolism and summarized as follows: Genetically obese mice (ob/ob) were fasted overnight. The compounds were administered orally via a stomach tube and each mouse serially bled from the orbital sinus at various times and the blood samples were analyzed for blood glucose. When the effects of the compounds on blood glucose levels were to be determined, glucose was administered orally at a rate of 2 g per kg. 30 minutes after administration of the test compound. Glucose in the blood was determined by the potassium ferricyanide potassium ferrocyanide oxidation reaction auto analyzer.

The latter method measures directly the amount of glucose in the blood at any given time and from this, the maximum percent decrease in blood sugar can be readily calculated and reported as hypoglycemic activity per se. In this way, the present compounds are shown to markedly improve glucose tolerance of non-anesthetized hyperglycemic mice when administered to them at dose levels as low as 10 mg/kg orally and lower fasting blood glucose levels when administered at dose levels as low as 30 mg/kg orally.

The instant invention is further described by the following examples which are intended to be merely descriptive and should not be construed as limitative of the invention.

EXAMPLE 1

Preparation of 6-Methyl-2-(1-piperazinyl)pyridine dihydrochloride (a) 2-[1-(4-BOC)piperazinyl]-6-methylpyridine 6-Chloro-2-picoline (2.5 g; 19.6 mmol) and 1-BOC-piperazine (15.0 g, 80.65 mmol) were intimately mixed and heated under nitrogen in a melt at 145° C. for 16 hours. Upon cooling, the dark residue was separated between 10% aq. $Na_2CO_3$ (150 mL) and $Et_2O$ (150 mL) and the aqueous layer was further washed with $Et_2O$ (2×150 mL). The cooled organic layers were dried ($MgSO_4$), filtered, and evaporated to dryness to give an amber syrup. This was purified on a silica gel column (3×33 cm) developed with pet ether-$Et_2O$ (4:1) fractions containing the required product, 2-[1-(4-BOC)-piperazinyl]-6-methylpyridine, were cooled and evaporated to a clear syrup which crystallized on standing. Mass spec-showed M+ at M/e 277.

(b) 6-Methyl-2-(1-piperazinyl)pyridine dihydrochloride

The product of step 1a (0.502 g; 1.81 mmol) was dissolved in CF₃COOH (25 mL) and allowed to stand at room temperature for 45 minutes. This solution was evaporated to dryness under a stream of nitrogen and the amber residue was dissolved in a little H₂O and passed onto a Dowex 1×2 (OH) column (2×42 cm) packed and developed in H₂O. Fractions containing the required product were pooled and evaporated to dryness in vacuo to give the title compound as free base. This syrup was dissolved in EtOH (5 mL) and methanolic HCl was added until the solution was acidic to pH paper. After evaporation of some solvent under a nitrogen stream, crystallization occurred and the solid was collected by centrifugation and the solid was collected by centrifugation and washed with Et₂O. Mass spec. showed M+ (free base) at M/e 177.

Calcd for $C_{10}H_{15}N_3.2HCl$: C, 48.01; H, 6.85; N, 16.80 Found: C, 48.07; H, 6.51; N, 16.88.

EXAMPLE 2

Preparation of 6-Methyl-2-[1-(4-methyl)piperazinyl]pyridine dihydrochloride

6-Chloro-2-picoline (2.31 g; 18.11 mmol) and N-methyl piperazine (10 mL) were mixed and heated under reflux, under nitrogen (oil-bath temperature 200° C.), for 24 hours. Upon cooling, and standing at room temperature for 60 hours; the mixture solidified and was dissolved in $CH_2Cl_2$ (50 mL). This solution was extracted with 10% aq. $Na_2CO_3$ (50 mL) and the aqueous layer was back-washed with $CH_2Cl_2$ (2×50 mL). The pooled organic phases were dried (MgSO₄), filtered, and evaporated to dryness to give 3.68 g of an amber syrup. This was purified by chromatography on a silica gel column (3×21 cm) developed first with $CH_2Cl_2$ (300 mL) and then with MeOH—$CH_2Cl_2$ (5:95) until completion. Fractions containing the required product were cooled and evaporated to give a clear syrup (1.62 g; 47%) which was converted to the dihydrochloride salt in the usual fashion by using EtOH (6 mL) and methanolic HCl (6 mL). Evaporation to dryness gave a white solid residue which was recrystallized from EtOH to give the titled compound. Mass spec. showed M+ (free base) at M/e 191.

Calcd for $C_{11}H_{17}N_3.2HCl$: C, 50.01; H, 7.25; N, 15.91 Found: C, 50.09; H, 7.09; N, 16.11

EXAMPLE 3

Preparation of 1-(2-pyridyl)-piperazine dimaleate

A solution of 465 mg. (0.004 mole) of maleic acid in 2 ml. of methanol was added to 327 mg. (0.002 mole) of 1-(2-pyridyl)-piperazine [K. L. Howard, H. W. Stewart, E. A. Conroy, ad J. J. Dentor, J. Org. Chem., 18, 1484 (1953)] in 1 ml. of methanol. The white solids which separated were recrystallized from methanol to yield 1-(2-pyridyl)-piperazine dimaleate, m.p. 140°–141° C.

Anal. Calcd. for $C_9H_{13}N_3.2C_4H_4O_4$: C, 51.64; H, 5.35; N, 10.63. Found: C, 52.00; H, 5.51; N, 11.00.

What is claimed is:

1. A composition useful for the treatment of diabetes or obesity with associated insulin resistance which comprises a inert carrier and a therapeutically effective amount of a compound having the formula (I):

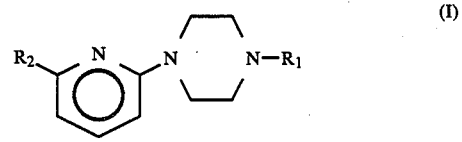

wherein:
$R_1 = C_{1-6}$alkyl, $C_{2-6}$alkenyl, or $C_{2-6}$alkynyl;
$R_2 = $H, $C_{1-6}$alkyl, $C_{2-6}$alkenyl, or $C_{2-6}$alkynyl.

2. A method for the treatment of diabetes or obesity with associated insulin resistance which comprises administering to a patient in need of such treatment a therapeutically effective amount of a compound having the formula (I):

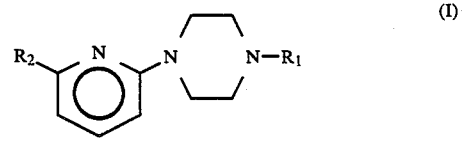

wherein:
$R_1 = C_{1-6}$alkyl, $C_{2-6}$alkenyl, $C_{2-6}$alkynyl;
$R_2 = $H, $C_{1-6}$alkyl, $C_{2-6}$alkenyl, or $C_{2-6}$alkynyl.

3. A compound of structural formula (I):

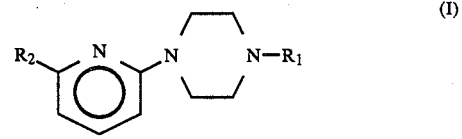

wherein:
$R_1 = C_{1-6}$alkyl, $C_{2-6}$alkenyl, or $C_{2-6}$alkynyl;
$R_2 = $H, $C_{1-6}$alkyl, $C_{2-6}$alkenyl, or $C_{2-6}$alkynyl.

4. A compound of claim 3 wherein:
$R_1$ is $C_{1-6}$alkyl;
$R_2$ is $C_{1-6}$alkyl.

5. A compound of claim 4 wherein:
$R_1$ is $CH_3$; and
$R_2$ is $CH_3$.

* * * * *